(12) United States Patent
Hara et al.

(10) Patent No.: US 9,717,858 B2
(45) Date of Patent: Aug. 1, 2017

(54) GASKET FOR PREFILLED SYRINGE AND PREFILLED SYRINGE

(71) Applicant: SUMITOMO RUBBER INDUSTRIES, LTD., Kobe-shi, Hyogo (JP)

(72) Inventors: Seiji Hara, Kobe (JP); Hiroaki Nakano, Kobe (JP); Hiroyuki Kaneko, Kobe (JP); Yasuhiko Kondo, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 291 days.

(21) Appl. No.: 14/613,049

(22) Filed: Feb. 3, 2015

(65) Prior Publication Data

US 2015/0231337 A1   Aug. 20, 2015

(30) Foreign Application Priority Data

Feb. 19, 2014   (JP) .................................. 2014-029602

(51) Int. Cl.
  *A61M 5/315*   (2006.01)
  *A61L 31/10*   (2006.01)
  *A61L 31/14*   (2006.01)

(52) U.S. Cl.
  CPC ......... *A61M 5/31513* (2013.01); *A61L 31/10* (2013.01); *A61L 31/14* (2013.01)

(58) Field of Classification Search
  CPC ...... A61M 5/31513; A61M 2205/0238; A61M 2205/0222; A61M 2005/3131
  See application file for complete search history.

(56) References Cited

U.S. PATENT DOCUMENTS

2011/0104085 A1* 5/2011 Klug ...................... A61K 8/898
                                                                         424/59
2015/0148748 A1* 5/2015 Shluzas ............... A61M 5/3221
                                                                         604/196

FOREIGN PATENT DOCUMENTS

JP         2005-185747 A         7/2005

\* cited by examiner

*Primary Examiner* — Emily Schmidt
(74) *Attorney, Agent, or Firm* — Birch, Stewart, Kolasch & Birch, LLP

(57) ABSTRACT

A gasket for prefilled syringe according to the present invention is a gasket for prefilled syringe that includes a fluid contacting portion, a sliding portion with a circumferential surface, a film layer made of a fluororesin coated on the fluid contacting portion and sliding portion and further, and a coating layer including trimethylsiloxysilicate laminated on the film layer covering the sliding portion.

12 Claims, 3 Drawing Sheets

GASKET FOR PREFILLED SYRINGE AND PREFILLED SYRINGE

CROSS-REFERENCE TO RELATED APPLICATIONS

The present application corresponds to Japanese Patent Application No. 2014-029602 filed on Feb. 19, 2014 in the Japan Patent Office, and the entire disclosure of this application is incorporated herein by reference.

FIELD OF THE INVENTION

The present invention relates to a gasket for prefilled syringe and a prefilled syringe having the gasket.

BACKGROUND ART

The use of prefilled syringes, which are filled with a medical fluid in advance, is spreading in recent years one to being excellent in usage convenience and enabling prevention of medical accidents such as mixing up of medical drugs.

With a prefilled syringe, a front end portion, on which an injection needle is to be mounted, is sealed by a cap. In using the prefilled syringe, an injection needle is mounted on the front end portion and the medical fluid can be administered via the injection needle by pushing in a plunger rod toward the front end side to slide a gasket.

Rubber members such as the gasket and cap used in the prefilled syringe are left in a state of directly contacting the medical fluid for a long period of time and therefore a butyl rubber based material, which is excellent in chemical resistance, gas permeation resistance, water vapor permeation, resistance, and aging resistance, is frequently used.

However, some medical drugs each as bioengineered formulations are at times affected adversely by the gasket or the nozzle cap due to interaction with matter eluted from raw material rubber and compounding agents of the rubber material or interaction due to detachment of a coating agent, etc.

Particularly, a front end surface portion of the gasket directly contacts the medical fluid filling the interior of a syringe barrel and it is of concern that components, etc., derived from the raw material rubber and compounding agents or the rubber material, may elute into the medical fluid from she gasket main body.

Also, although low in possibility of direct contact with the medical fluid, a sliding portion of the gasket that contacts an inner peripheral surface of the syringe barrel has been coated with an oil type or a curable type silicone as a lubricant for the purpose of improving the sliding property with respect to the barrel inner surface in a process of fitting the gasket into the barrel or in a process of pushing the plunger during medical fluid injection. There are thus cases where the silicone migrates to the medical fluid as foreign matter and, depending on the medical fluid, adversely affect the quality of the medical fluid. Particularly, a silicone coating agent of an amount greater than that coated on the gasket is coated on the syringe barrel inner peripheral surface in many cases, and the influence is also made large by the largeness of fluid contact area with respect to the medical fluid filling the interior of the syringe barrel.

Therefore in recent years, a product, with which a fluororesin film of excellent chemical resistance is laminated on an outer side of a gasket main body, constituted of an elastic body of butyl rubber, etc., to secure safety of the formulation, has been developed and has been proposed as a laminated gasket for use in a syringe made of glass or a prefilled syringe made of resin.

As the fluororesin film to be laminated, tetrafluoroethylene-ethylene copolymer (ETFE), polytetrafluoroethylene (PTFE), polychlorotetrafluoroethylene (PCTFE), tetrafluoroethylene-perfluoroalkylvinyl ether copolymer (PFA), or copolymer of tetrafluoroethylene and a trace amount of perfluoroalkoxide (modified PTFE), etc., is appropriate.

Among the above, polytetrafluoroethylene (PTFE), which has the lowest frictional coefficient, is frequently used in particular from the standpoint of reducing sliding resistance with respect to a syringe barrel inner surface.

By the proposed arrangement, elution of rubber components into the chemical fluid from the gasket front end surface portion in direct contact with the medical fluid can be prevented and further, the sliding resistance of a gasket side surface portion (circumferential surface portion) in contact with the syringe barrel inner surface can be decreased. Coating of a large amount of silicone coating agent on the syringe barrel inner surface is thus made unnecessary and contamination of the medical fluid by the barrel inner surface due to detachment of silicone can also be prevented. That is, by laminating the fluororesin film at least on an outer surface of the gasket main body, the medical fluid filling the interior of the syringe is made higher in safety.

Further, a process of coating the syringe barrel inner surface with a large amount of silicone can be omitted to provide a merit of enabling the cost of syringe set assembly to be reduced.

BRIEF SUMMARY OF THE INVENTION

However, the following issue arises with the method of laminating the fluororesin film on the gasket outer surface.

In comparison to a conventional gasket made of rubber, with the gasket laminated with one fluororesin film, a resin that undergoes plastic deformation is laminated on the outer side of the elastic body made of butyl based rubbery thermoplastic elastomer, etc., that constitutes the gasket main body. A gasket sliding portion in contact with the inner surface of the syringe barrel made of glass or resin is thereby decreased in rubber elasticity and degraded in airtightness. There thus arises the issue of possibility of leakage of the medical fluid.

Even when an annular projecting portion (circumferential surface portion) of the gasket is increased in seal width (contact width) to improve on the fluid leakage, this does not provide any effects of improving the airtightness or fluidtightness, and with a method of increasing the diameter of the annular projecting portion (circumferential surface portion) and thereby increasing the compression ratio, it becomes difficult to fit the gasket into the syringe barrel.

Further, there arise such problems as wrinkling of the laminated fluororesin film at the gasket annular seal portion, etc. In addition, there also arises the issue that the piston is increased in sliding resistance value.

The present invention has been made to resolve the above issues and an object thereof is to provide a gasket for prefilled syringe that can further increase the stability and safety of a medical fluid filling the interior of a syringe and yet is improved in medical fluid sealing performance.

An embodiment of the present invent for provides a gasket for prefilled syringe that includes a fluid contacting portion and a sliding portion with a circumferential surface and where a film layer made of a fluororesin is coated on the fluid contacting portion and the sliding portion and further, a coating layer including trimethylsiloxysilicate is laminated on the film layer covering the sliding portion.

In the embodiment of the present invention, the film layer is selected from the group consisting of tetrafluoroethylene-ethylene copolymer (ETFE), polytetrafluoroethylene (PTFE), polychlorotetrafluoroethylene (PCTFE), tetrafluoroethylene-perfluoroalkylvinyl ether copolymer (PFA), and copolymer of tetrafluoroethylene and a trace amount of perfluoroalkoxide (modified PTFE).

In the embodiment of the present invention, the coating layer includes a mixture of trimethylsiloxysilicate and dimethylpolysiloxane.

In the embodiment of the present invention, the mixture of trimethylsiloxysilicate and dimethylpolysiloxane is such that a mixing ratio of the two components trimethylsiloxysilicate/dimethylpolysiloxane=5/95 to 30/70 weight %.

In the embodiment of the present invention, a kinematic viscosity of the dimethylpolysiloxane in the mixture is in a range of 20 to 1000 centistokes (cst, mm$^2$/s).

An embodiment of the present invention provides a prefilled syringe including a syringe barrel with a tubular shape, a plunger combined with the syringe barrel and capable of moving reciprocally reside the syringe barrel, and the gasket mounted on a front end of the plunger.

With the embodiment of the present invention, wrinkling of the fluororesin film that occurs in a process of fitting or sliding the gasket in the syringe barrel can be suppressed to prevent leakage of a medical fluid filling the interior of the syringe barrel.

Specifically, wrinkling of the fluororesin film is suppressed and the coating layer constituted of trimethylsiloxysilicate fills minute gaps between the fluororesin film and an inner surface of the syringe barrel to prevent leakage of the medical fluid.

That is, with the embodiment of the present invention, the following two objects can be achieved reliably by laminating the fluororesin film on the outer peripheral surface of the gasket main body.
(1) By covering with the elation of rubber components into the medical fluid from a gasket front end surface portion in direct contact with the medical fluid can be prevented.
(2) Sliding resistance of a gasket side surface portion (circumferential surface portion) in contact with the syringe barrel inner surface can be decreased without occurrence of leakage of medical fluid from surfaces of contact of the gasket and the syringe barrel. The coating of a large amount of a silicone coating agent on the syringe barrel inner surface can thus be abolished.

DETAILED DESCRIPTION OF EMBODIMENT

An embodiment of the present invention shall now be described specifically with reference to the drawings.

Figure 1:
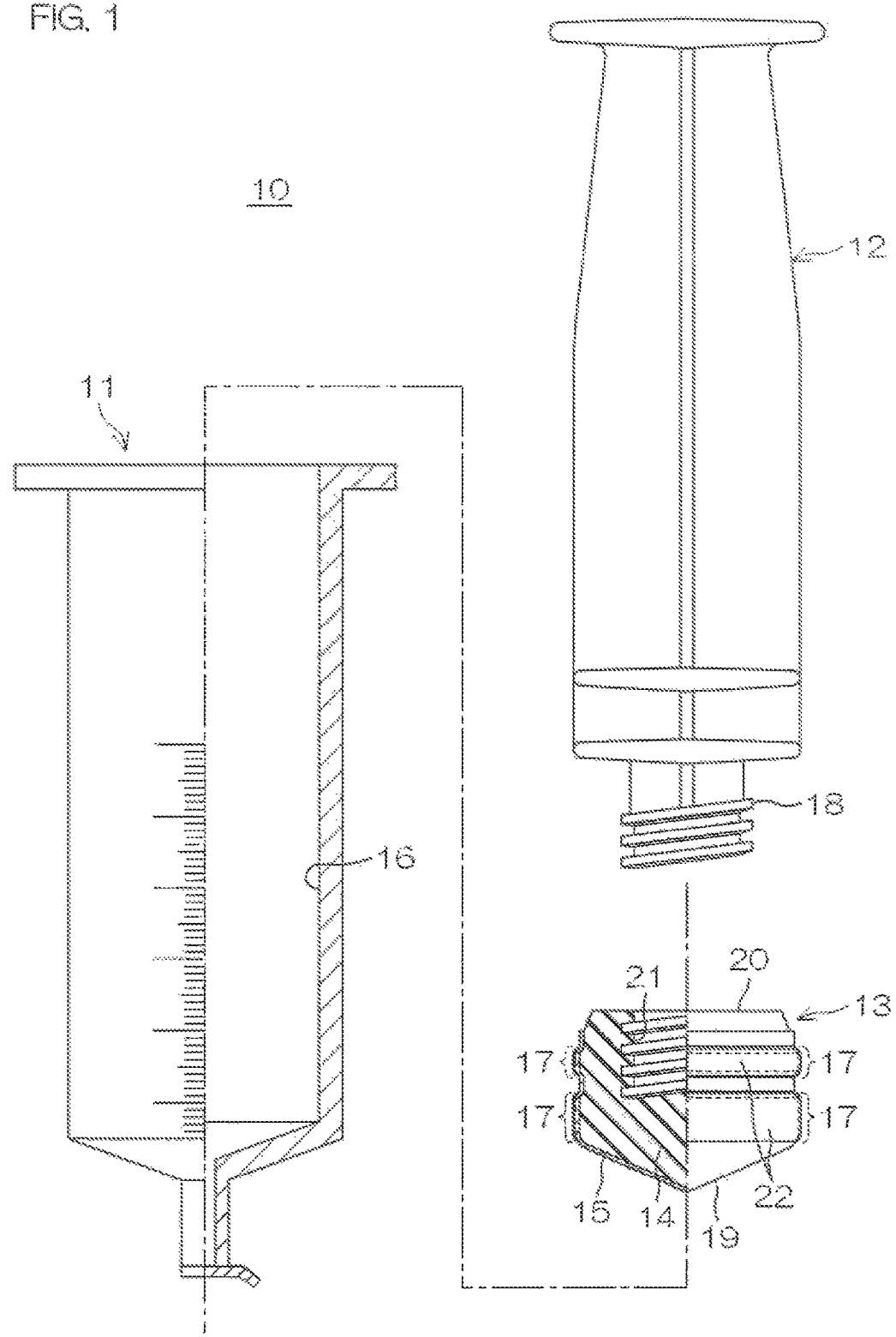
FIG. 1 is a drawing of a medical syringe according to an embodiment of the present invention in a disassembled state.

FIG. 1 is a drawing showing, in a disassembled state, a medical syringe according to an embodiment of the present invention, which is a syringe that is a so-called prefilled syringe. In FIG. 1, respective halves of a syringe barrel 11 and a gasket 13 are shown in sectional view.

With reference to FIG. 1, the prefilled syringe 10 includes syringe barrel 11 of cylindrical shape, a plunger 12 combined with the syringe barrel 11 and capable of moving reciprocally inside the syringe barrel 11, and the gasket 13 mounted on a front end of the plunger 12. The gasket 13 is a so-called laminated gasket that includes a main body 14 constituted of an elastic material (rubber or elastomer, etc.) and a laminated film 15 laminated on a surface of the main body 14. The gasket 13 includes two circumferential surface portions 17 that contact an inner peripheral surface 16 of the syringe barrel 11 in airtight and fluid-tight manner.

The plunger 12 is constituted, for example, of a resin plate piece with a cross-shaped transverse section and has, at its front end portion, a head portion 18, onto which the gasket 13 is mounted. The head portion 18 is made of resin integral with the plunger 12 and is processed to a male screw shape.

The gasket 13 has substantially cylindrically shape having a short axis and a front end surface 19 thereof has, for example, an obtuse conical shape with a projecting axial center portion. It has a fitting recess portion 21 of female screw shape engraved in an axial direction from its rear end surface 20. The gasket 13 is mounted on the front end of the plunger 12 by the head portion 18 of the plunger 12 being screwed into the fitting recess portion 21.

Figure 2:
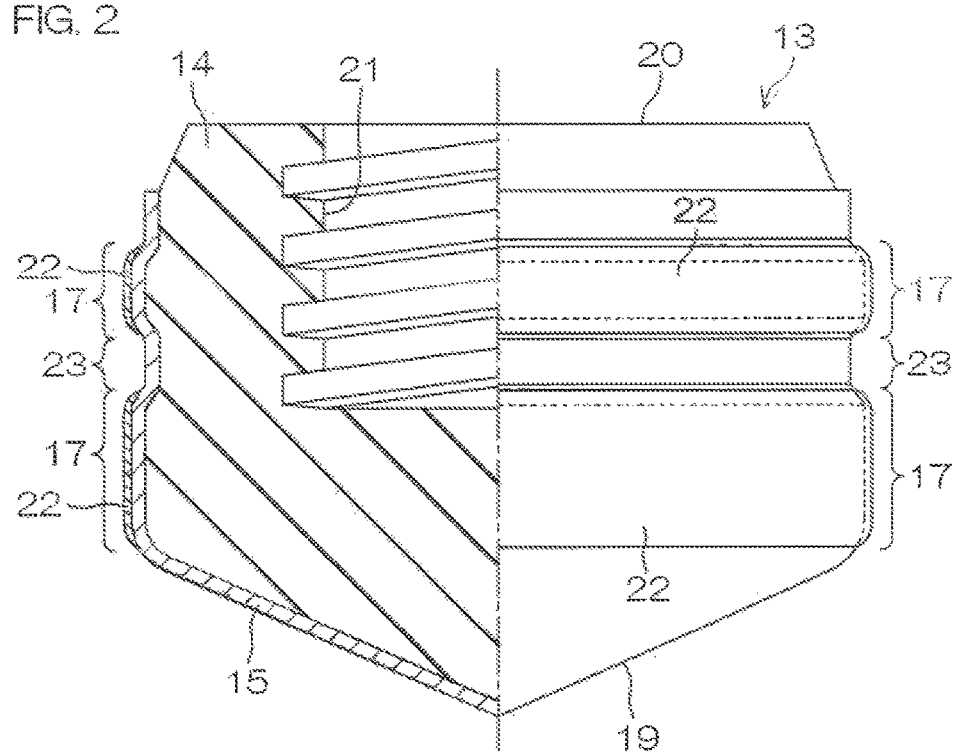
FIG. 2 is a drawing of a laminated gasket according to an embodiment of the present invention, showing half of the gasket in sectional view.

FIG. 2 is a magnified drawing of just the gasket 13 shown in FIG. 1 and shows half of the gasket 13 in sectional view.

The arrangement of the gasket 13 according to the present embodiment shall now be described in more detail with reference to FIG. 2.

The gasket 13 includes a main body 14 and a laminated film 15 laminated on a surface of the main body 14. The main body 14 is made of an elastic material and the material thereof is not restricted in particular. For example, it may be made of a thermosetting rubber or a thermoplastic elastomer. Among these, a thermosetting rubber or, among thermoplastic elastomers, a dynamic crosslinked thermoplastic elastomer having crosslinking points is more preferable due to being excellent in heat resistance. Such polymer components are also not restricted in particular, and for example, ethylene-propylene-diene rubber and butadiene rubber, which are excellent in molding properties, are preferable. Butyl rubber, chlorinated butyl rubber, and brominated butyl rubber, which are excellent in gas permeation resistance, are also preferable.

The laminated film 15 laminated on the surface of the main body 14 is not particularly restricted in type as long as it is a firm that can prevent the transfer of components from crosslinked rubber (the main body 14) and is better in sliding property than rubber, that is, lower in frictional coefficient than rubber. A film of ultrahigh molecular weight polyethylene or fluorine based resin that is of proven record in medical applications can be cited as an example. Among these, a fluorine based resin is preferable in being excellent in sliding property and excellent in chemical stability of the surface. Any known resin that contains fluorine may be used as the fluorine based resin and PTFE, modified PTFE, ethylene-tetrafluoroethylene copolymer (ETFE), perfluoroalkyl ether (PFA), etc., can be cited as examples. PTFE and modified PTFE are preferable in being excellent in both sliding property and chemical stability. ETFE is preferable in being high in resistance to γ-ray sterilization. From a standpoint of adhesion to the main body 14, a film constituted of a mixture or a laminate of such resins may also be used.

Characteristics of the laminated gasket 13 according to the present embodiment are that it includes the circumferential surface portions 17 as annular projecting portions that contact the inner peripheral surface 16 of the syringe barrel 11 in airtight and fluid-tight manner and that a coating layer 22, which contains trimethylsiloxysilicate, is further laminated on surfaces of the laminated film 13 disposed on the surfaces of the circumferential surface portions 17. The coating layer 22 is preferably laminated just on the surfaces of the laminated film 15 at the circumferential surface portions 13 and is not laminated at portions besides the surfaces of the circumferential surface portions 17.

Although in the present embodiment, the two circumferential surface portions 17 of a front side circumferential surface portion 17 and a rear side circumferential surface portion 17 are provided, just one or three or more of the circumferential surface portions 17 may be provided instead. In this case, the coating layer 22 is not formed and the laminated film 15 may be exposed at an annular recess portion 23 formed between the front side circumferential surface portion 17 and the rear side circumferential surface portion 17. Also, the shape of the gasket is not restricted to the shape of the present embodiment.

The present invention shall now be described in further detail by way of examples. The present invention is not restricted by the following examples.

EXAMPLES (1) Sample Preparation

Vulcanized molded products, each having a fluorine based film laminated on an outer periphery of a gasket main body having a butyl based rubber as a main component, were prepared. The size of each gasket is that suitable for a 1 milliliter syringe.

Although the fluorine based film laminated on the gasket main body outer periphery is selected from the group consisting of tetrafluoroethylene-ethylene copolymer (ETFE), polytetrafluoroethylene (PTFE), polychlorotetrafluoroethylene (PCTFE), tetrafluoroethylene-perfluoroalkylvinyl ether copolymer (PFA), and copolymer of tetrafluoroethylene and a trace amount of perfluoroalkoxide (modified PTFE), PTFE, which is the lowest in frictional coefficient, was used in the examples.

Coating layers of silicone, respectively laminated on sliding portions (the circumferential surface portions 17 of FIG. 2) of the respective butyl based rubber gaskets laminated with the fluorine based films, were prepared by the method described below.

Each of the various types of silicone shown in Table 1 was dissolved in ethyl acetate.

The amount of silicone dissolved in ethyl acetate was adjusted so that the silicone concentration was 1 wt % of the solution as a whole.

TABLE 1

| | Name of silicone compound/Mixing ratio | Kinematic viscosity of dimethylpolysiloxane (mm2/S, 25° C.) |
|---|---|---|
| Comparative Example 1 | None | |
| Comparative Example 2 | Dimethylpolysiloxane | 1000 |
| Comparative Example 3 | Dimethylpolysiloxane | 10000 |
| Comparative Example 4 | Fluorine-modified methylpolysiloxane | |
| Comparative Example 5 | Amino-modified methylpolysiloxane | |
| Comparative Example 6 | Methylphenylpolysiloxane | |
| Example 1 | Trimethylsiloxysilicate (100%)/dimethylpolysiloxane (0%) | — (solid powder) |
| Example 2 | Trimethylsiloxysilicate (60%)/dimethylpolysiloxane (40%) | 1000 |
| Example 3 | Trimethylsiloxysilicate (30%)/dimethylpolysiloxane (70%) | 1000 |
| Example 4 | Trimethylsiloxysilicate (15%)/dimethylpolysiloxane (85%) | 1000 |
| Example 5 | Trimethylsiloxysilicate (5%)/dimethylpolysiloxane (95%) | 1000 |
| Example 6 | Trimethylsiloxysilicate (2%)/dimethylpolysiloxane (98%) | 1000 |
| Example 7 | Trimethylsiloxysilicate (15%)/dimethylpolysiloxane (85%) | 5 |
| Example 8 | Trimethylsiloxysilicate (15%)/dimethylpolysiloxane (85%) | 20 |
| Example 9 | Trimethylsiloxysilicate (15%)/dimethylpolysiloxane (85%) | 100 |
| Example 10 | Trimethylsiloxysilicate (15%)/dimethylpolysiloxane (85%) | 8000 |
| Example 11 | Trimethylsiloxysilicate (15%)/dimethylpolysiloxane (85%) | 12000 |

With the respective butyl based rubber gaskets laminated with the fluorine based films, the sliding portions (the circumferential surface portions 17 that are the annular projecting portions) in contact with the barrel inner surfaces were respectively immersed in the respective types of solutions prepared and thereafter dried at room temperature in air to volatilize the ethyl acetate solvent and fix the silicone onto the gasket outer peripheral portions. With each of the ethyl acetate solutions, the fluid amount per single gasket was set to 3.6 μL/gasket. With the above process, the amount of silicone attached per single gasket is adjusted to be in a range of 10 to 1000 μg/gasket and preferably 10 to 200 μg/gasket.

(2) Fluid Leakage Evaluation Method (A). Preparation of Aqueous Solution for Fluid Leakage Evaluation An aqueous solution was prepared by adding the surfactant, polysorbate 80 (polyoxyethylene sorbitan oleate) to water to achieve a concentration of 0.1%, and this was colored in red by further adding a red food coloring to 0.15% to enable fluid leakage to be observed more easily.

(B). Fitting of the Gasket into the Syringe Barrel and Filling with the Aqueous Solution Each prepared sample was fitted in a 1 milliliter barrel, the material of which is COP resin, so that the gasket front end was positioned at a position 13 mm from the rear end of the barrel.

After fitting, the barrel was filled with approximately 1 milliliter of the aqueous solution prepared by the method described in (A) from the front end side until the interior of the barrel became full with the aqueous solution, and after then fitting a nozzle cap onto the barrel top, the barrel was left still for four days at 40° C. with the barrel front end side facing upward to put the aqueous solution in contact with the gasket.

(C). Observation of Fluid Leakage

Four days after filling with the aqueous solution, leakage into a recess portion of the gasket (recess portion between the front end annular rib and the rear annular rib) was observed at a magnification of 50 times. For each specification, twenty samples were observed and a leakage percentage was determined from the number of samples that leaked.

(Example) If 10 out of the 20 samples leaked, the fluid leakage percentage is 50%.

(3) Sliding Property Evaluation Method (A). Fitting of the Gasket into the Syringe Barrel Each prepared sample was fitted in a 1 milliliter barrel, the material of which is COP resin, so that the gasket front end was positioned at a position 13 mm from the rear end of the barrel.

The interior of the barrel was not filled with the aqueous solution and each barrel was subject to the sliding test in the empty state.

(B). Sliding Test

After fitting the screw at the front end of the plunger to the screw in the interior of gashes fitted into the barrel interior, an autograph was used to press and move the plunger in the direction of the barrel front end and the resistance force in this process was detected by a load cell.

Plunger moving speed: 100 mm/min
Plunger moving distance: 25 mm

Figure 3:
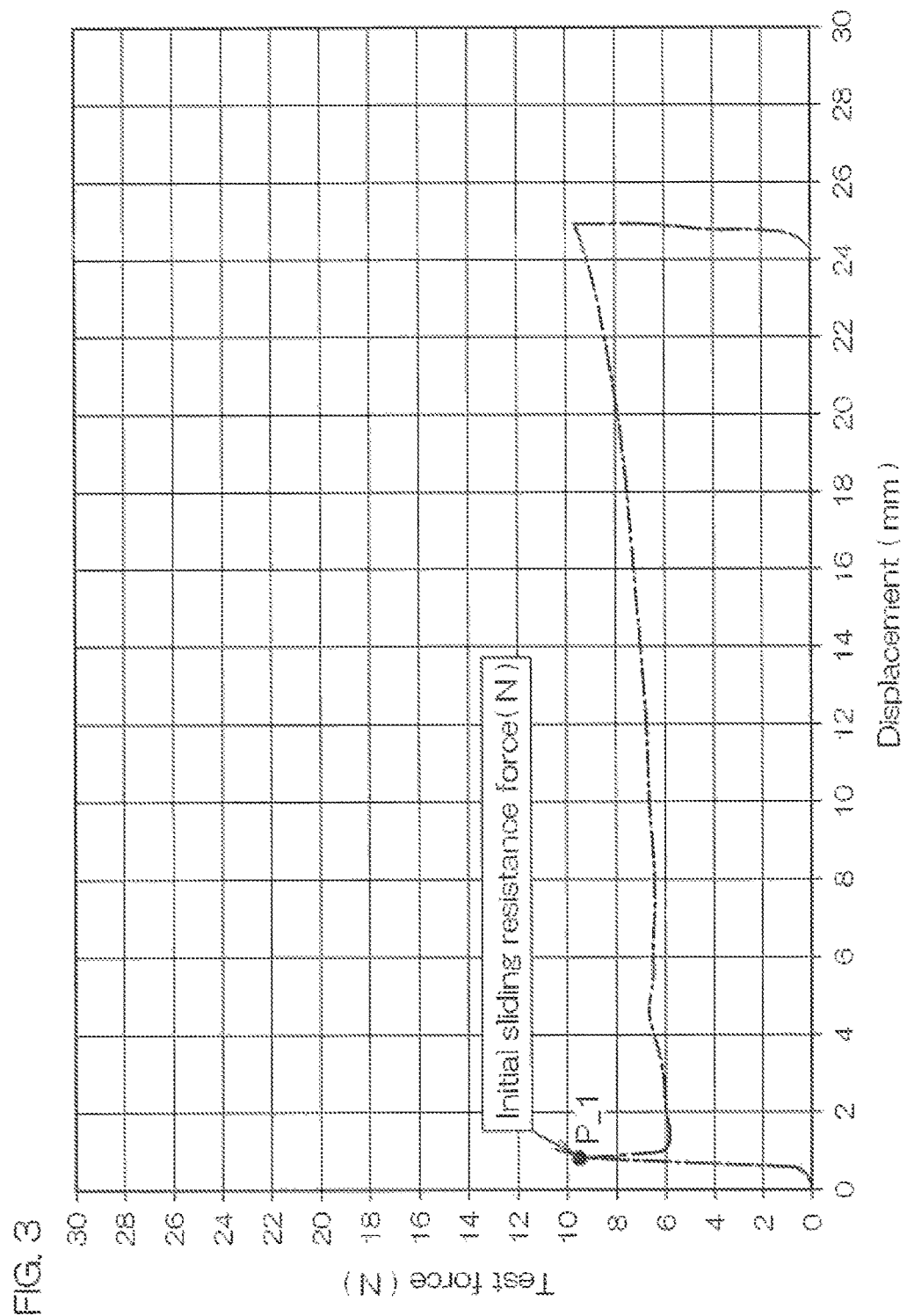
FIG. 3 is a diagram of a relationship between a test method and measurement values of a sliding test.

When the movement of the gasket is started, from the stationary state, the resistance rises rapidly and the resistance force at that point was detected and determined as an initial sliding resistance force (N). The test was performed on two samples of each specification and the determined value was indicated as an average for n=2. This is shown in FIG. 3.

(4) Evaluation Results

The evaluation results are shown in Table 2.

TABLE 2

|  | Fluid leakage evaluation Fluid leakage percentage after elapse of four days (%) | Initial sliding resistance force (N) |
|---|---|---|
| Comparative Example 1 | 100 | 14.3 |
| Comparative Example 2 | 100 | 7.0 |
| Comparative Example 3 | 95 | 6.7 |
| Comparative Example 4 | 100 | 7.2 |
| Comparative Example 5 | 80 | 6.0 |
| Comparative Example 6 | 95 | 7.1 |
| Example 1 | 20 | 40.0 |
| Example 2 | 10 | 23.3 |
| Example 3 | 10 | 9.9 |
| Example 4 | 5 | 8.5 |
| Example 5 | 10 | 7.9 |
| Example 6 | 15 | 7.4 |
| Example 7 | 10 | 2.9 |
| Example 8 | 5 | 3.7 |
| Example 9 | 5 | 5.1 |
| Example 10 | 10 | 10.3 |
| Example 11 | 15 | 12.8 |

It can be understood that Examples 1 to 11, which are within the scope of claims 1 to 3, are extremely low in fluid leakage percentage and excellent in comparison to Comparative Examples 1 to 6 that fall outside the scope of the claims.

Also, with respect to the rise of initial sliding resistance in Examples 1 and 2, it was possible to reduce the initial sliding resistance by increasing the mixing ratio of dimethylpolysiloxane to decrease the viscosity of the mixture (Examples 3 to 11).

That is, with the mixture of trimethylsiloxysilicate and dimethylpolysiloxane, it was possible to adjust the sliding resistance to be in an appropriate range by adjusting the mixing ratio of the two components to adjust the viscosity of the mixture.

From the above results, it can be said that Examples 3 to 11 do not compromise the proper object of laminating the make it unnecessary to coat a large amount of a silicone coating agent, etc., on the inner surface of the syringe barrel.

In particular, with Examples 3 to 5 and 7 to 11, which have specifications indicated in claim 4, and Examples 3 to 6 and 8 to 10, which have specifications indicated in claim 5, it was possible to meet the antinomic required characteristics of preventing fluid leakage and enabling reduction of sliding resistance at the same time.

The invention claimed is:

1. A gasket for prefilled syringe comprising:
   a fluid contacting portion;
   a sliding portion with a circumferential surface;
   a film layer made of a fluororesin coated on the fluid contacting portion and the sliding portion; and
   a coating layer including trimethylsiloxysilicate laminated on the film layer covering the sliding portion, wherein
   the coating layer includes a mixture of trimethylsiloxysilicate and dimethylpolysiloxane.

2. The gasket for prefilled syringe according to claim 1, wherein the film layer is selected from the group consisting of tetrafluoroethylene-ethylene copolymer (ETFE), polytetrafluoroethylene (PTFE), polychlorotetrafluoroethylene (PCTFE), tetrafluoroethylene-perfluoroalkylvinyl ether copolymer (PFA), and copolymer of tetrafluoroethylene and a trace amount of perfluoroalkoxide (modified PTFE).

3. The gasket for prefilled syringe according to claim 1, wherein the mixture of trimethylsiloxysilicate and dimethylpolysiloxane is such that a mixing ratio of the two components trimethylsiloxysilicate/dimethylpolysiloxane=5/95 to 30/70 weight %.

4. The gasket for prefilled syringe according to claim 3, wherein a kinematic viscosity of the dimethylpolysiloxane in the mixture is in a range of 20 to 10000 centistokes (cst, mm$^2$/s).

5. The gasket for prefilled syringe according to claim 1, wherein the sliding portion includes an annular projecting portion selectively formed on the circumferential surface, and the coating layer is selectively formed only on the film layer covering the annular projecting portion.

6. The gasket for prefilled syringe according to claim 5, wherein the annular projecting portion includes at least a front side projecting portion at a front end side of the gasket and a rear side projection portion disposed further to the rear side than the front side projecting portion.

7. A prefilled syringe comprising:
   a syringe barrel with a tubular shape;
   a plunger combined with the syringe barrel and capable of moving reciprocally inside the syringe barrel; and
   a gasket mounted on a front end of the plunger; and
   wherein the gasket includes a fluid contacting portion,
   a sliding portion with a circumferential surface,
   a film layer made of a fluororesin coated on the fluid contacting portion and the sliding portion, and a coating layer including trimethylsiloxysilicate laminated on the film layer covering the sliding portion, and the coating layer includes a mixture of trimethylsiloxysilicate and dimethylpolysiloxane.

8. The prefilled syringe according to claim 7, wherein the film layer is selected from the group consisting of tetrafluoroethylene-ethylene copolymer (ETFE), polytetrafluoroethylene (PTFE), polychlorotetrafluoroethylene (PCTFE), tetrafluoroethylene-perfluoroalkylvinyl ether copolymer (PFA), and copolymer of tetrafluoroethylene and a trace amount of perfluoroalkoxide (modified PTFE).

9. The prefilled syringe according to claim 7, wherein the mixture of trimethylsiloxysilicate and dimethylpolysiloxane is such that a mixing ratio in weight % of the two components trimethylsiloxysilicate/dimethylpolysiloxane is in the range 5/95 to 30/70.

10. The prefilled syringe according to claim 9, wherein a kinematic viscosity of the dimethylpolysiloxane in the mixture is in a range of 20 to 10000 centistokes (cst, $mm^2/s$).

11. The prefilled syringe according to claim 7, wherein the sliding portion includes an annular projecting portion formed selectively on the circumferential surface and in airtight and fluid-tight contact with an inner peripheral surface of the syringe barrel, and the coating layer is selectively formed only on the film layer covering the annular projecting portion.

12. The prefilled syringe according to claim 11, wherein the annular projecting portion includes at least a front side projecting portion at a front end side of the gasket and a rear side projection portion disposed further to the rear side than the front side projecting portion.

* * * * *